US011667656B2

(12) United States Patent
Souza et al.

(10) Patent No.: US 11,667,656 B2
(45) Date of Patent: Jun. 6, 2023

(54) CRYSTALLINE FORMS OF TENOFOVIR ALAFENAMIDE

(71) Applicant: Apotex Inc., Toronto (CA)

(72) Inventors: Fabio E. S. Souza, Brantford (CA); Avedis Karadeolian, Brantford (CA); Alexander J. Stirk, Brantford (CA)

(73) Assignee: Apotex Inc., Toronto (CA)

( * ) Notice: Subject to any disclaimer, the term of this patent is extended or adjusted under 35 U.S.C. 154(b) by 179 days.

(21) Appl. No.: 17/159,238

(22) Filed: Jan. 27, 2021

(65) Prior Publication Data

US 2022/0235079 A1 Jul. 28, 2022

(51) Int. Cl.
*C07F 9/6561* (2006.01)
*A61K 45/06* (2006.01)

(52) U.S. Cl.
CPC .......... *C07F 9/65616* (2013.01); *A61K 45/06* (2013.01); *C07B 2200/13* (2013.01)

(58) Field of Classification Search
CPC .................................................. C07B 2200/13
See application file for complete search history.

(56) References Cited

U.S. PATENT DOCUMENTS

| 10,155,781 B2 | 12/2018 | Shi et al. |
| 2002/0119443 A1 | 8/2002 | Becker et al. |
| 2013/0065856 A1 | 3/2013 | Liu et al. |
| 2016/0122373 A1 | 5/2016 | Rao et al. |

FOREIGN PATENT DOCUMENTS

| CN | 105237571 B | 3/2018 |
| WO | 0208241 A2 | 1/2002 |
| WO | 2013025788 A1 | 2/2013 |
| WO | 2014195724 A1 | 12/2014 |
| WO | 2015040640 A2 | 3/2015 |
| WO | 2015107451 A2 | 7/2015 |
| WO | 2015176602 A1 | 11/2015 |
| WO | 2016192692 A1 | 12/2016 |
| WO | 2016205141 A1 | 12/2016 |

OTHER PUBLICATIONS

Bernstein, "Polymorphism in Molecular Crystals", 2002, pp. 9-10, Oxford University Press Inc., New York.
Porter, "Coating of Pharmaceutical Dosage Forms", Remington: The Science and Practice of Pharmacy, 2006, pp. 929-938, 21st Edition, Lippincott Williams & Wilkins, Philadelphia.
Rudnic et al., "Oral Solid Dosage Forms", Remington: The Science and Practice of Pharmacy, 2006, pp. 889-928, 21st Edition, Lippincott Williams & Wilkins, Philadelphia.
Stahl et al., "Handbook of Pharmaceutical Salts: Properties, Selection, and Use", International Union of Pure and Applied Chemistry (IUPAC), 2002, pp. 330-345, Wiley-Vch, Weinheim.

*Primary Examiner* — John S Kenyon
(74) *Attorney, Agent, or Firm* — The Webb Law Firm

(57) ABSTRACT

The present invention provides novel crystalline forms of tenofovir alafenamide comprising tenofovir alafenamide and two different pharmaceutically acceptable acids, compositions and processes for the preparation thereof, and their use in the treatment of a human immunodeficiency virus (HIV) infection or a hepatitis B virus (HBV) infection.

20 Claims, 10 Drawing Sheets

CRYSTALLINE FORMS OF TENOFOVIR ALAFENAMIDE

BACKGROUND OF THE INVENTION

Field of the Invention

The present invention is directed to novel crystalline forms of tenofovir alafenamide, pharmaceutical compositions containing these forms, processes for their preparation, and their use in the treatment of a human immunodeficiency virus (HIV) infection or a hepatitis B virus (HBV) infection.

Description of Related Art

Tenofovir alafenamide (1), or L-alanine, N—[(S)-[[(1 R)-2-(6-amino-9H-purin-9-yl)-1-methylethoxy]methyl]phenoxyphosphinyl]-, 1-methylethyl ester, in the form of a hemifumarate, is the active ingredient in VEMLIDY®, which is indicated for the treatment of chronic hepatitis B virus (HBV) infection in adults with compensated liver disease. Further combination drug products which also comprise Tenofovir alafenamide hemifumarate include GENVOYA®, ODEFSEY®, and DESCOVY®, which are indicated for the treatment of human immunodeficiency virus (HIV-1) infections.

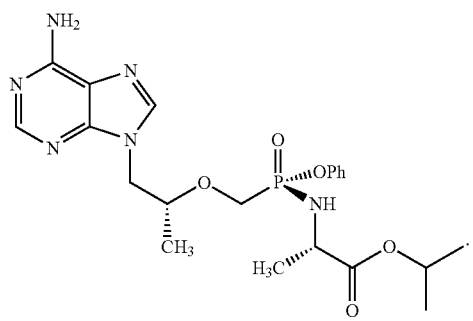

(1)

Crystalline forms of tenofovir alafenamide, including co-crystals and salts, are reported in, for example, WO 2002/008241 A2, WO 2013/025788 A1, WO 2014/195724 A1, WO 2015/040640 A2, WO 2015/107451 A2, WO 2015/176602 A1, WO 2016/192692 A1, WO2016/205141 A1, and CN 105237571 B.

According to the review published by the U.S. Center for Drug Evaluation and Research (CDER) in connection with the approval of GENVOYA® (NDA 207561), the drug substance tenofovir alafenamide hemifumarate has high solubility but low permeability, placing it in Class III of the Biopharmaceutics Classification System (BCS).

Different crystalline forms of the same compound, including co-crystals and salts, may have different crystal packing, thermodynamic, spectroscopic, kinetic, surface and mechanical properties. For example, different crystalline forms may have different stability properties such that a particular crystalline form may be less sensitive to heat, relative humidity (RH) and/or light. Different crystalline forms of a compound may also be more susceptible to moisture uptake, resulting in a potential alteration of physical characteristics of the form such as flowability, density or compressibility, which can lead to problems during formulation/tabletting and/or to changes in dissolution rate of the formulated drug product.

For example, unintended absorption of moisture by a hygroscopic crystalline form of a drug substance can alter its compressibility during tabletting, resulting in a softer tablet having a faster dissolution rate following administration. A particular crystalline form may provide more favourable compressibility and/or density properties, thereby providing more desirable characteristics for formulation and/or product manufacturing. Differences in stability between solid forms of a drug may result from changes in chemical reactivity, such as differential oxidation. Such properties may provide for more suitable product qualities, including a dosage form that is more resistant to discolouration when comprised of a specific crystalline form.

Particular crystalline forms may also have different solubilities, thereby providing different pharmacokinetic parameters, which allow for specific crystalline forms to be used in order to achieve specific pharmacokinetic targets. Crystalline forms which incorporate a co-former molecule or a counterion such as co-crystals and salts, may be imparted with properties arising from novel interactions between the compound and the co-former or counterion such as differences in permeability or solubility. Differences in permeability between crystalline forms are particularly relevant for compounds exhibiting low permeability, such as BCS Class III drug substances, where even a modest increase in permeability can provide a beneficial enhancement in bioavailability. For example, in CN 105237571 B, tenofovir alafenamide hemisuccinate was shown to have improved physicochemical parameters in comparison to tenofovir alafenamide hemifumarate when administered to rats, such as higher maximum plasma concentration (Cmax) and absorption (AUC).

Although general approaches to crystalline form screening of active pharmaceutical ingredients are known, it is well established that the prediction of the properties, or suitable methods for the preparation of, any given crystalline form is not possible (Joel Bernstein, *Polymorphism in Molecular Crystals*, Oxford University Press, New York, 2002, page 9).

Owing to the reported low bioavailability of tenofovir alafenamide, there exists a need for novel crystalline forms of tenofovir alafenamide having improved properties for use in providing drug products containing tenofovir alafenamide, and commercially amenable processes for their manufacture.

SUMMARY OF THE INVENTION

The tenofovir alafenamide crystalline forms of the present invention comprise tenofovir alafenamide having two different pharmaceutically acceptable acids in the same crystal lattice. The novel tenofovir alafenamide crystalline forms of the present invention incorporate more than one type of acid molecule, which provides a unique opportunity to alter the properties of tenofovir alafenamide to suit a particular need. For example, embodiments of the crystalline forms of tenofovir alafenamide of the present invention that incorporate both fumaric acid and succinic acid exhibit a higher aqueous dissolution rate compared to crystalline forms of tenofovir alafenamide comprising fumaric acid or succinic acid alone. Further, by altering the relative molar composition of succinic acid and fumaric acid in the crystal structure, a variety of aqueous dissolution rates can be achieved. Indeed, it is expected that varying the relative proportions of each acid component in a given crystalline form of tenofovir alafenamide of the present invention will have an impact on numerous properties of the crystalline form.

Furthermore, the present invention provides crystalline forms of tenofovir alafenamide that can be prepared by efficient and industrially compatible processes.

Accordingly, in a first aspect of the present invention, there is provided a crystalline form of tenofovir alafenamide succinate fumarate comprising tenofovir alafenamide, succinic acid and fumaric acid. Preferably, in the crystalline form of the first aspect, the molar ratio of tenofovir alafenamide to (succinic acid+fumaric acid) is approximately 1:1. More preferably, the crystalline form of the first aspect is represented by the formula [TAF][succinic acid]$_{1-x}$[fumaric acid]$_x$ wherein TAF is tenofovir alafenamide and x is in the range of 0.05 to 0.95. In a further preferred embodiment of the first aspect, the formula of the crystalline form is selected from the group consisting of [TAF][succinic acid]$_{0.9}$[fumaric acid]$_{0.1}$, [TAF][succinic acid]$_{0.8}$[fumaric acid]$_{0.2}$, [TAF][succinic acid]$_{0.75}$[fumaric acid]$_{0.25}$, [TAF][succinic acid]$_{0.7}$[fumaric acid]$_{0.3}$, [TAF][succinic acid]$_{0.6}$[fumaric acid]$_{0.4}$, [TAF][succinic acid]$_{0.5}$[fumaric acid]$_{0.5}$, [TAF][succinic acid]$_{0.4}$[fumaric acid]$_{0.6}$, [TAF][succinic acid]$_{0.3}$[fumaric acid]$_{0.7}$, [TAF][succinic acid]$_{0.25}$[fumaric acid]$_{0.75}$, [TAF][succinic acid]$_{0.2}$[fumaric acid]$_{0.8}$ and [TAF][succinic acid]$_{0.1}$[fumaric acid]$_{0.9}$. Preferably, the crystalline form of the first aspect has a formula selected from the group consisting of [TAF][succinic acid]$_{0.25}$[fumaric acid]$_{0.75}$, [TAF][succinic acid]$_{0.5}$[fumaric acid]$_{0.5}$ and [TAF][succinic acid]$_{0.75}$[fumaric acid]$_{0.25}$. In a further preferred embodiment of the first aspect, the molar ratio of tenofovir alafenamide to succinic acid to fumaric acid is approximately 1:0.25:0.75. In this further preferred embodiment of the first aspect, the crystalline form is characterized by a PXRD diffractogram comprising peaks, expressed in degrees 2θ (±0.2°), at 5.6°, 10.5° and 22.4°. Preferably, in this embodiment of the first aspect, the PXRD diffractogram further comprises at least three peaks, expressed in degrees 2θ (±0.2°), selected from the group consisting of: 9.4°, 9.7°, 11.1°, 11.5°, 13.3°, 14.1°, 16.9°, 17.6°, 19.1° and 28.2°. Further preferred in this embodiment of the first aspect is that the PXRD diffractogram further comprises peaks, expressed in degrees 2θ (±0.2°), at 9.4°, 9.7°, 11.1°, 11.5°, 13.3°, 14.1°, 16.9°, 17.6°, 19.1° and 28.2°. Further preferred in this embodiment of the crystalline form of the first aspect is that the PXRD diffractogram comprises peaks in substantially the same positions (±0.2° 2θ) as those shown in FIG. 1. Preferably, in this embodiment of the first aspect, the crystalline form is characterized by a DSC thermogram comprising an endothermic peak with a peak onset at approximately 119° C. and a peak maximum at approximately 120° C. Further preferred in this embodiment of the first aspect is that the crystalline form is characterized by a DSC thermogram that is substantially the same in appearance as the DSC thermogram provided in FIG. 5. In another preferred embodiment of the first aspect, the molar ratio of tenofovir alafenamide to succinic acid to fumaric acid is approximately 1:0.5:0.5. In this further preferred embodiment of the first aspect, the crystalline form is characterized by a PXRD diffractogram comprising peaks, expressed in degrees 2θ (±0.2°), at 5.6°, 10.5° and 22.2°. Preferably, in this embodiment of the first aspect, the PXRD diffractogram further comprises at least three peaks, expressed in degrees 2θ (±0.2°), selected from the group consisting of: 7.2°, 9.4°, 9.7°, 11.1°, 11.5°, 13.2°, 14.1°, 16.7°, 18.9° and 27.8°. Further preferred in this embodiment of the first aspect is that the PXRD diffractogram further comprises peaks, expressed in degrees 2θ (±0.2°), at 7.2°, 9.4°, 9.7°, 11.1°, 11.5°, 13.2°, 14.1°, 16.7°, 18.9° and 27.8°. Further preferred in this embodiment of the crystalline form of the first aspect is that the PXRD diffractogram comprises peaks in substantially the same positions (±0.2° 2θ) as those shown in FIG. 2. Preferably, in this embodiment of the first aspect, the crystalline form is characterized by a DSC thermogram comprising an endothermic peak with a peak onset at approximately 118° C. and a peak maximum at approximately 120° C. Further preferred in this embodiment of the first aspect is that the crystalline form is characterized by a DSC thermogram that is substantially the same in appearance as the DSC thermogram provided in FIG. 6. In another preferred embodiment of the first aspect, the molar ratio of tenofovir alafenamide to succinic acid to fumaric acid is approximately 1:0.75:0.25. In this further preferred embodiment of the first aspect, the crystalline form is characterized by a PXRD diffractogram comprising peaks, expressed in degrees 2θ (±0.2°), at 5.5°, 10.5° and 22.3°. Preferably, in this embodiment of the first aspect, the PXRD diffractogram further comprises at least three peaks, expressed in degrees 2θ (±0.2°), selected from the group consisting of: 7.2°, 9.3°, 9.7°, 11.1°, 11.5°, 13.2°, 14.1°, 16.8°, 19.0° and 28.1°. Further preferred in this embodiment of the first aspect is that the PXRD diffractogram further comprises peaks, expressed in degrees 2θ (±0.2°), at 7.2°, 9.3°, 9.7°, 11.1°, 11.5°, 13.2°, 14.1°, 16.8°, 19.0° and 28.1°. Further preferred in this embodiment of the crystalline form of the first aspect is that the PXRD diffractogram comprises peaks in substantially the same positions (±0.2° 2θ) as those shown in FIG. 3. Preferably, in this embodiment of the first aspect, the crystalline form is characterized by a DSC thermogram comprising an endothermic peak with a peak onset at approximately 118° C. and a peak maximum at approximately 120° C. Further preferred in this embodiment of the first aspect is that the crystalline form is characterized by a DSC thermogram that is substantially the same in appearance as the DSC thermogram provided in FIG. 7.

In a second aspect of the present invention, there is provided a crystalline form of tenofovir alafenamide succinate malate comprising tenofovir alafenamide, succinic acid and L-malic acid. In a preferred embodiment of the second aspect, the molar ratio of tenofovir alafenamide to succinic acid to L-malic acid is approximately 1:0.4:0.4. In a further preferred embodiment of the second aspect, the crystalline form is characterized by a PXRD diffractogram comprising peaks, expressed in degrees 2θ (±0.2°), at 5.4°, 9.9° and 15.1°. Preferably, in this embodiment of the second aspect, the PXRD diffractogram further comprises at least three peaks, expressed in degrees 2θ (±0.2°), selected from the group consisting of: 11.8°, 13.2°, 13.9°, 16.5°, 19.0°, 21.1°, 22.0° and 26.1°. Further preferred in this embodiment of the second aspect is that the PXRD diffractogram further comprises peaks, expressed in degrees 2θ (±0.2°), at 11.8°, 13.2°, 13.9°, 16.5°, 19.0°, 21.1°, 22.0° and 26.1°. Further preferred in this embodiment of the crystalline form of the second aspect is that the PXRD diffractogram comprises peaks in substantially the same positions (±0.2° 2θ) as those shown in FIG. 4. Preferably, in this embodiment of the second aspect, the crystalline form is characterized by a DSC thermogram comprising an endothermic peak with a peak onset at approximately 119° C. and a peak maximum at approximately 120° C. Further preferred in this embodiment of the second aspect is that the crystalline form is characterized by a DSC thermogram that is substantially the same in appearance as the DSC thermogram provided in FIG. 8.

In a third aspect of the present invention, there is provided a pharmaceutical composition comprising a crystalline form of tenofovir alafenamide succinate fumarate according to the first aspect, or tenofovir alafenamide succinate malate according to the second aspect, and one or more pharmaceutically acceptable excipients. Preferably, the pharmaceutical composition is in the form of a solid oral dosage form. Most preferably, the pharmaceutical composition is a tablet. In a further preferred embodiment of the third aspect, the pharmaceutical composition comprises an additional therapeutic agent, preferably selected from the group consisting of HIV protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors. More preferably, the additional therapeutic agent is selected from the group consisting of emtricitabine, darunavir, cobicistat, bictegravir and rilpivirine. Preferably, the pharmaceutical composition of the third aspect comprises an amount of the crystalline form of tenofovir alafenamide succinate fumarate or tenofovir alafenamide succinate malate of the first or second aspects that is equivalent to 10 mg or 25 mg tenofovir alafenamide free base.

In a fourth aspect of the present invention, there is provided the use of a crystalline form of tenofovir alafenamide succinate fumarate according to the first aspect or tenofovir alafenamide succinate malate according to the second aspect, in the treatment of a human immunodeficiency virus (HIV) infection or a hepatitis B virus (HBV) infection. In a further preferred embodiment of the fourth aspect, the tenofovir alafenamide succinate fumarate or the tenofovir alafenamide succinate malate is used in combination with an additional therapeutic agent, preferably selected from the group consisting of HIV protease inhibiting compounds, HIV nonnucleoside inhibitors of reverse transcriptase, HIV nucleoside inhibitors of reverse transcriptase, HIV nucleotide inhibitors of reverse transcriptase, HIV integrase inhibitors, and CCR5 inhibitors. More preferably, the additional therapeutic agent is selected from the group consisting of emtricitabine, darunavir, cobicistat, bictegravir and rilpivirine.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

Figure 1:
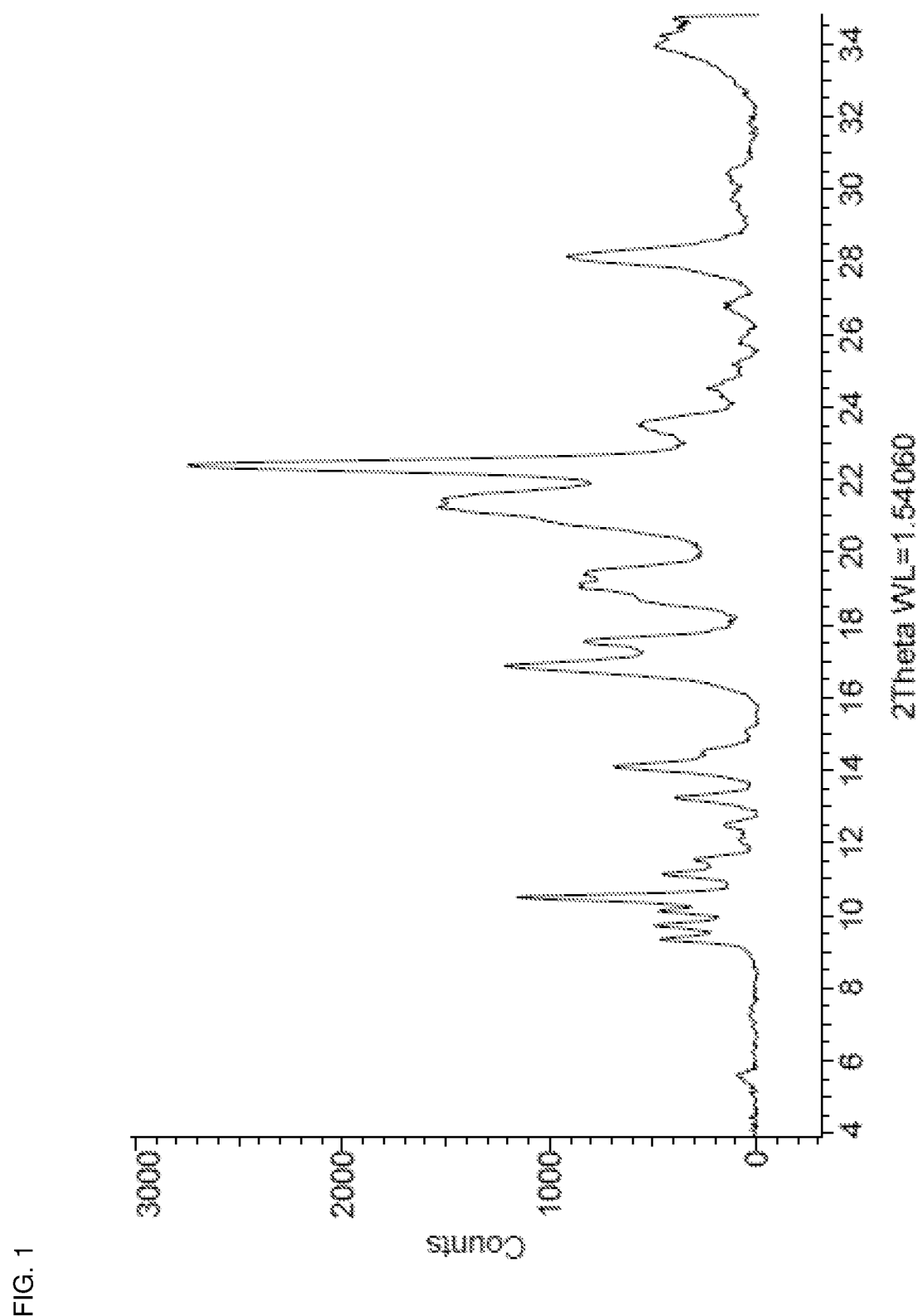
FIG. 1 is a representative PXRD diffractogram of tenofovir alafenamide succinate fumarate (1:0.25:0.75) as prepared in Example 1.

The tenofovir alafenamide crystalline forms of the present invention comprise tenofovir alafenamide having two different pharmaceutically acceptable acids in the same crystal lattice. This surprising result, in which two similar but distinct acids are incorporated together with tenofovir alafenamide to afford a novel and uniform crystalline form, provides unique opportunities to modify the properties of tenofovir alafenamide. For example, crystalline tenofovir alafenamide succinate fumarate (1:0.5:0.5) of the present invention exhibits a higher intrinsic dissolution rate (IDR) compared to crystalline tenofovir alafenamide fumarate (1:1) or tenofovir alafenamide succinate (1:1).

The tenofovir alafenamide crystalline forms of the present invention comprise two different acids selected from the group consisting of fumaric acid, succinic acid, and L-malic acid. According to P. Heinrich Stahl, Camille G. Wermuth (Eds.), Handbook of Pharmaceutical Salts Properties, Selection, and Use; 2002, which is an oft-cited authority on the pharmaceutical acceptability of salts, such acids qualify as first class acids. First class acids are classified by Stahl as those that afford physiologically ubiquitous ions or metabolites in biochemical pathways, supporting their unrestricted use in pharmaceuticals. Generally, according to Stahl, first class acids, such as those incorporated into the tenofovir alafenamide crystalline forms of the present invention are preferable to second and third class acids, which may invite more regulatory scrutiny when used in pharmaceutical applications.

The tenofovir alafenamide crystalline forms of the present invention exhibit differences in properties when compared to the known crystalline forms of tenofovir alafenamide. Properties that differ between the invention and known crystalline forms of tenofovir alafenamide include crystal packing properties such as molar volume, density and hygroscopicity; thermodynamic properties such as melting point and solubility; kinetic properties such as dissolution rate and chemical/polymorphic stability; surface properties such as crystal habit/particle morphology; and/or mechanical properties such as hardness, tensile strength, compactibility, tabletting, handling, flow, and blending.

Depending on the manner in which the embodiments of the invention are prepared, the methodology and instrument used for PXRD analysis, the intensity of a given peak observed in a PXRD diffractogram of a crystalline form may vary when compared to the same peak in the representative PXRD diffractograms provided in FIGS. 1 to 4. Thus, differences in relative peak intensities between peaks in a PXRD diffractogram for a given crystalline form may be observed when compared to the relative peak intensities of the peaks in the representative PXRD diffractograms of FIGS. 1 to 4. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1 to 4, it is understood that individual peak positions may vary between ±0.2° 2θ from the values observed in the representative PXRD diffractograms provided in FIGS. 1 to 4 for the crystalline forms of the invention, or listed in Tables 1 to 4. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1 to 4. Thus, PXRD diffractograms of the crystalline forms of the present invention may, in some circumstances, display the same relative peak positions as observed in the representative PXRD diffractograms provided in FIGS. 1 to 4, with the exception that each peak is offset in the same direction, and by approximately the same amount, such that the overall PXRD diffractogram is substantially the same in appearance as a PXRD diffractogram of FIGS. 1 to 4, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1 to 4.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermograms provided in FIGS. 5 to 8 and described herein. Such variations are known and understood by a person of skill in the art, and any such variations do not depart from the invention disclosed herein.

As used herein, the term 'crystalline form' refers to a substance with a particular arrangement of components in its crystal lattice, and which may be identified by physical characterization methods such as PXRD and/or DSC. The crystalline forms of tenofovir alafenamide of the present invention are multiple-component forms, which incorporate two different acid molecules into the crystal lattice with tenofovir alafenamide. Using techniques such as NMR spectroscopy, combined with PXRD and DSC, the crystalline forms of the present invention can be characterized as uniform crystalline forms that are distinguishable from physical mixtures of the components. In the crystalline forms of the present invention, identification of the exact nature of the bonding arrangement between tenofovir alafenamide, the first acid molecule, and the second acid molecule, whether ionic or non-covalent, for example, is not elucidated by definitive methods such as single crystal X-ray diffraction. In some embodiments of the present invention, the crystalline forms of tenofovir alafenamide maintain a similar crystal structure to that of a 'parent' crystalline form of tenofovir alafenamide with a single type of acid, such as tenofovir alafenamide succinate (1:1). For example, embodiments of crystalline forms of tenofovir alafenamide succinate fumarate comprising both succinic acid and fumaric acid exhibit PXRD reflections that are similar (isomorphous) to those of parent crystalline form tenofovir alafenamide succinate (1:1). NMR spectroscopy and DSC facilitate further characterization of the novel crystalline forms of the present invention.

Multi-component crystalline forms comprising more than one type of molecule may have some variability in the exact molar ratio of their components depending on a variety of conditions used. For example, a molar ratio of components within a multi-component crystalline form provides a person of skill in the art information as to the general relative quantities of the components of the crystalline form. In many cases, the molar ratio may vary by ±20% from a stated range. For example, with respect to the present invention, a molar ratio of 1:1 should be understood to include the ratios 1:0.8 and 1:1.2, as well as all of the individual ratios in between.

As used herein, TAF refers to tenofovir alafenamide.

As used herein, the term "room temperature" refers to a temperature in the range of 20° C. to 25° C.

Unless defined otherwise herein, the term "approximately", when used in reference to molar ratios, allows for a variance of plus or minus 10%.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a crystalline form of tenofovir alafenamide succinate fumarate comprising (i) tenofovir alafenamide; (ii) succinic acid; and (iii) fumaric acid, wherein the molar ratio of tenofovir alafenamide to (succinic acid+fumaric acid) is approximately 1:1.

In this embodiment of the present invention, the molar ratio of tenofovir alafenamide to the sum total of succinic acid and fumaric acid is approximately 1:1. Preferably, the crystalline form is represented by the formula [TAF][succinic acid]$_{1-x}$[fumaric acid]$_x$, wherein x is in the range of 0.05 to 0.95. Preferably, the crystalline form is represented by a formula selected from the group consisting of [TAF][succinic acid]$_{0.9}$[fumaric acid]$_{0.1}$, [TAF][succinic acid]$_{0.8}$[fumaric acid]$_{0.2}$, [TAF][succinic acid]$_{0.75}$[fumaric acid]$_{0.25}$, [TAF][succinic acid]$_{0.7}$[fumaric acid]$_{0.3}$, [TAF][succinic acid]$_{0.6}$[fumaric acid]$_{0.4}$, [TAF][succinic acid]$_{0.5}$[fumaric acid]$_{0.5}$, [TAF][succinic acid]$_{0.4}$[fumaric acid]$_{0.6}$, [TAF][succinic acid]$_{0.3}$[fumaric acid]$_{0.7}$, [TAF][succinic acid]$_{0.25}$[fumaric acid]$_{0.75}$ [TAF][succinic acid]$_{0.2}$[fumaric acid]$_{0.8}$ and [TAF][succinic acid]$_{0.1}$[fumaric acid]$_{0.9}$. More preferably, the crystalline form is represented by a formula selected from the group consisting of [TAF][succinic acid]$_{0.75}$[fumaric acid]$_{0.25}$, [TAF][succinic acid]$_{0.5}$[fumaric acid]$_{0.5}$, and [TAF][succinic acid]$_{0.25}$[fumaric acid]$_{0.75}$. Most preferably, the crystalline form is represented by the formula [TAF][succinic acid]$_{0.5}$[fumaric acid]$_{0.5}$.

In a second embodiment of the present invention, there is provided a crystalline form of tenofovir alafenamide, tenofovir alafenamide succinate fumarate Form APO-I, comprising tenofovir alafenamide, succinic acid, and fumaric acid in a molar ratio of approximately 1:0.25:0.75, respectively.

Tenofovir alafenamide succinate fumarate Form APO-I can be characterized by a PXRD diffractogram comprising, among other peaks, characteristic peaks, expressed in degrees 2θ (±0.2°), at 5.6°, 10.5° and 22.4°. Preferably, the PXRD diffractogram further comprises at least three peaks, expressed in degrees 2θ (±0.2°), selected from the group consisting of 9.4°, 9.7°, 11.1°, 11.5°, 13.3°, 14.1°, 16.9°, 17.6°, 19.1° and 28.2°. More preferably, the PXRD diffractogram further comprises peaks, expressed in degrees 2θ (±0.2°), at 9.4°, 9.7°, 11.1°, 11.5°, 13.3°, 14.1°, 16.9°, 17.6°, 19.1° and 28.2°.

An illustrative PXRD diffractogram of tenofovir alafenamide succinate fumarate Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the tenofovir alafenamide succinate fumarate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of tenofovir alafenamide succinate fumarate Form APO-I from FIG. 1

| Angle (2θ) | Relative intensity (%) |
|---|---|
| 5.61 | 3.6 |
| 9.35 | 16.8 |
| 9.73 | 17.8 |
| 10.13 | 17.0 |
| 10.50 | 41.9 |
| 11.14 | 16.4 |
| 11.54 | 11.1 |
| 12.50 | 5.7 |
| 13.25 | 14.3 |
| 14.10 | 25.1 |
| 16.88 | 44.1 |
| 17.55 | 30.3 |
| 19.13 | 31.2 |
| 21.25 | 56.0 |
| 22.39 | 100.0 |
| 28.15 | 33.4 |

Figure 5:
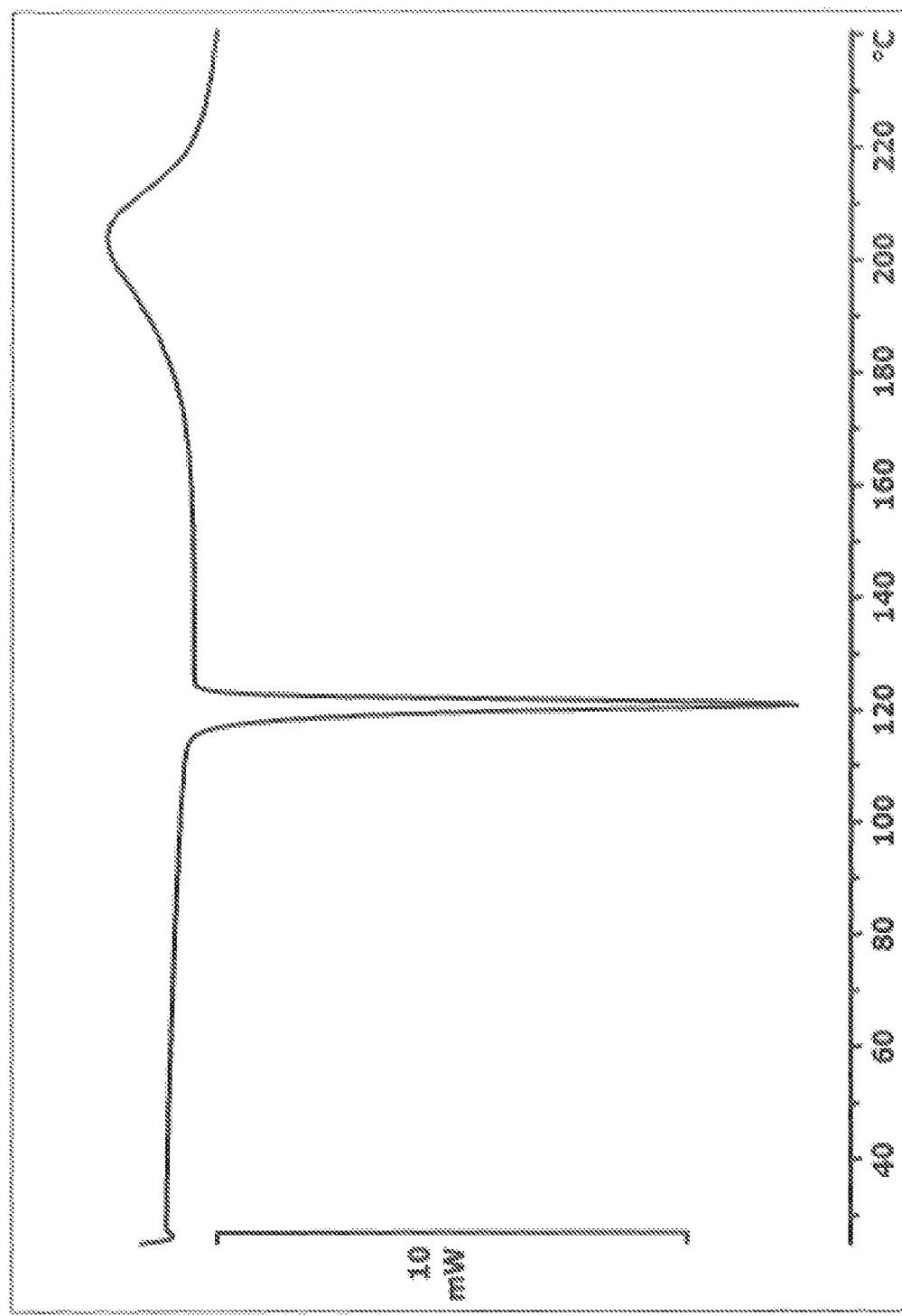
FIG. 5 is a representative DSC thermogram of tenofovir alafenamide succinate fumarate (1:0.25:0.75) as prepared in Example 1.

An illustrative DSC thermogram of tenofovir alafenamide succinate fumarate Form APO-I is shown in FIG. 5. The DSC thermogram may be further characterized by an endothermic peak with a peak onset at approximately 119° C. and a peak maximum at approximately 120° C.

In a third embodiment of the present invention, there is provided a crystalline form of tenofovir alafenamide, tenofovir alafenamide succinate fumarate Form APO-II, comprising tenofovir alafenamide, succinic acid, and fumaric acid in a molar ratio of approximately 1:0.5:0.5, respectively.

Tenofovir alafenamide succinate fumarate Form APO-II can be characterized by a PXRD diffractogram comprising, among other peaks, characteristic peaks, expressed in degrees 2θ (±0.2°), at 5.6°, 10.5° and 22.2°. Preferably, the PXRD diffractogram further comprises at least three peaks, expressed in degrees 2θ (±0.2°), selected from the group consisting of 7.2°, 9.4°, 9.7°, 11.1°, 11.5°, 13.2°, 14.1°, 16.7°, 18.9° and 27.8°. More preferably, the PXRD diffractogram further comprises peaks, expressed in degrees 2θ (±0.2°), at 7.2°, 9.4°, 9.7°, 11.1°, 11.5°, 13.2°, 14.1°, 16.7°, 18.9° and 27.8°. PXRD studies of capped and uncapped samples of tenofovir alafenamide succinate fumarate Form APO-II maintained in a 40° C./75% relative humidity (RH) stability chamber for at least 3 months showed that no change in the crystalline form occurred.

Figure 2:
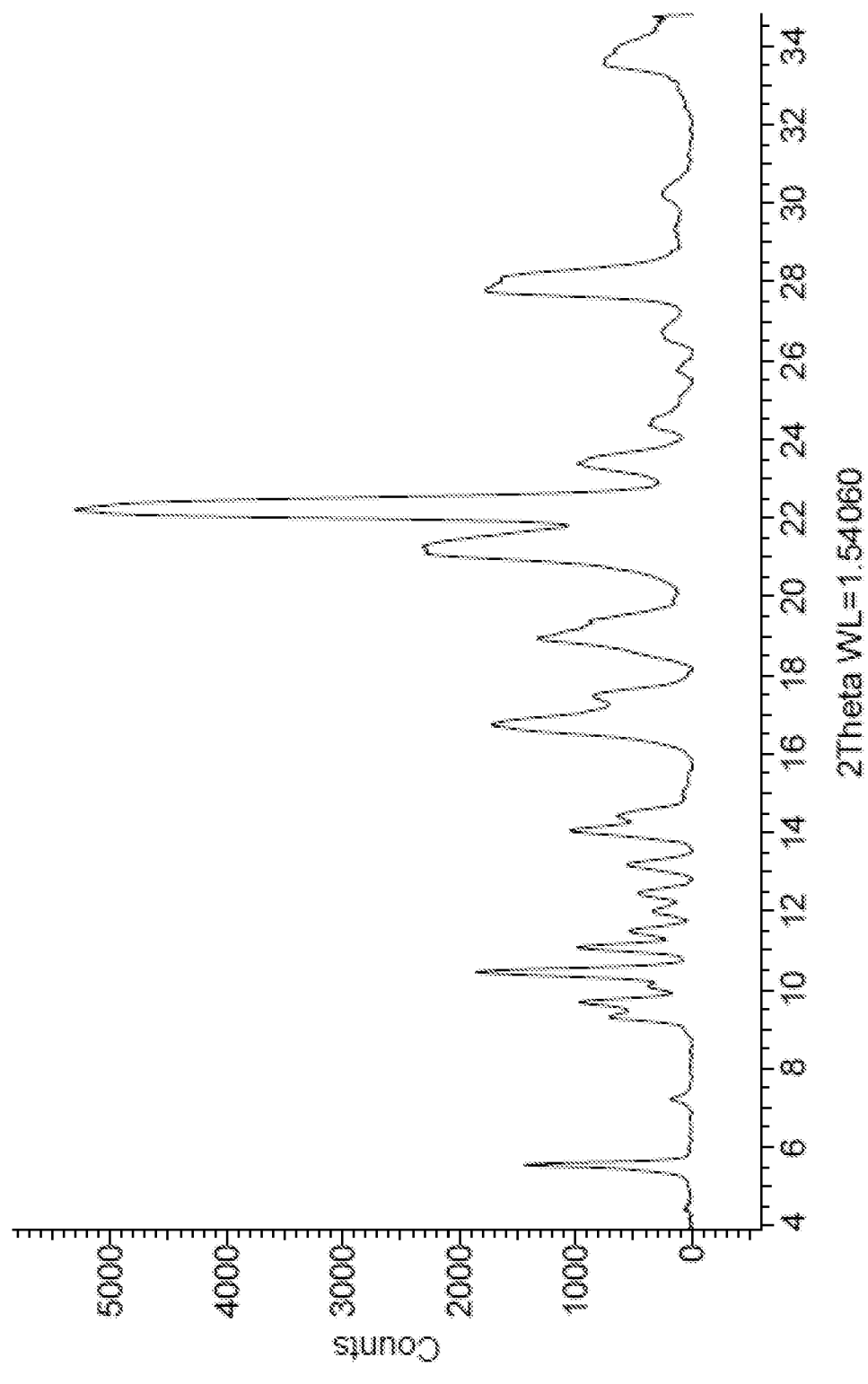
FIG. 2 is a representative PXRD diffractogram of tenofovir alafenamide succinate fumarate (1:0.5:0.5) as prepared in Example 2.

An illustrative PXRD diffractogram of tenofovir alafenamide succinate fumarate Form APO-II, as prepared in Example 2, is shown in FIG. 2. A peak listing, comprising representative peaks from the PXRD diffractogram in FIG. 2, and their relative intensities, is provided in Table 2. Although illustrative of the PXRD diffractogram that is provided for the tenofovir alafenamide succinate fumarate Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of tenofovir alafenamide succinate fumarate Form APO-II from FIG. 2

| Angle (2θ) | Relative intensity (%) |
|---|---|
| 5.55 | 27.0 |
| 7.23 | 3.4 |
| 9.38 | 12.1 |
| 9.68 | 18.2 |
| 10.45 | 34.9 |
| 11.08 | 18.6 |
| 11.49 | 10.2 |
| 12.01 | 6.2 |
| 12.45 | 8.7 |
| 13.19 | 10.5 |
| 14.05 | 19.7 |
| 14.42 | 12.1 |
| 16.74 | 32.4 |
| 17.47 | 16.0 |
| 18.94 | 25.1 |
| 21.27 | 43.5 |
| 22.22 | 100.0 |
| 27.81 | 33.3 |

Figure 6:
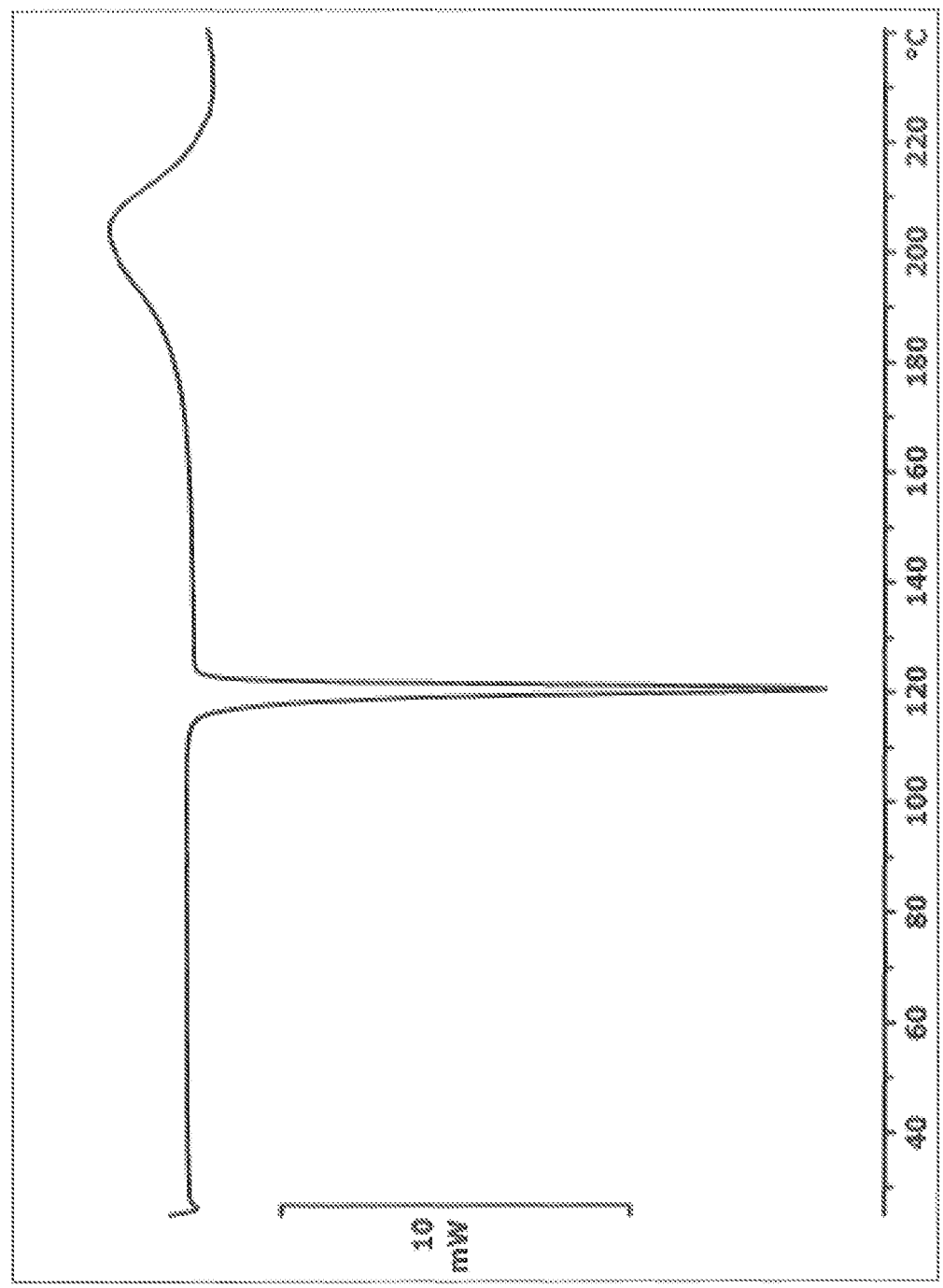
FIG. 6 is a representative DSC thermogram of tenofovir alafenamide succinate fumarate (1:0.5:0.5) as prepared in Example 2.

An illustrative DSC thermogram of tenofovir alafenamide succinate fumarate Form APO-II is shown in FIG. 6. The DSC thermogram may be further characterized by an endothermic peak with a peak onset at approximately 118° C. and a peak maximum at approximately 120° C.

In a fourth embodiment of the present invention, there is provided a crystalline form of tenofovir alafenamide, tenofovir alafenamide succinate fumarate Form APO-III, comprising tenofovir alafenamide, succinic acid and fumaric acid in a molar ratio of approximately 1:0.75:0.25, respectively.

Tenofovir alafenamide succinate fumarate Form APO-III can be characterized by a PXRD diffractogram comprising, among other peaks, characteristic peaks, expressed in degrees 2θ (±0.2°), at 5.5°, 10.5° and 22.3°. Preferably, the PXRD diffractogram further comprises at least three peaks, expressed in degrees 2θ (±0.2°), selected from the group consisting of 7.2°, 9.3°, 9.7°, 11.1°, 11.5°, 13.2°, 14.1°, 16.8°, 19.0° and 28.1°. More preferably, the PXRD diffractogram further comprises peaks, expressed in degrees 2θ (±0.2°), at 7.2°, 9.3°, 9.7°, 11.1°, 11.5°, 13.2°, 14.1°, 16.8°, 19.0° and 28.1°.

Figure 3:
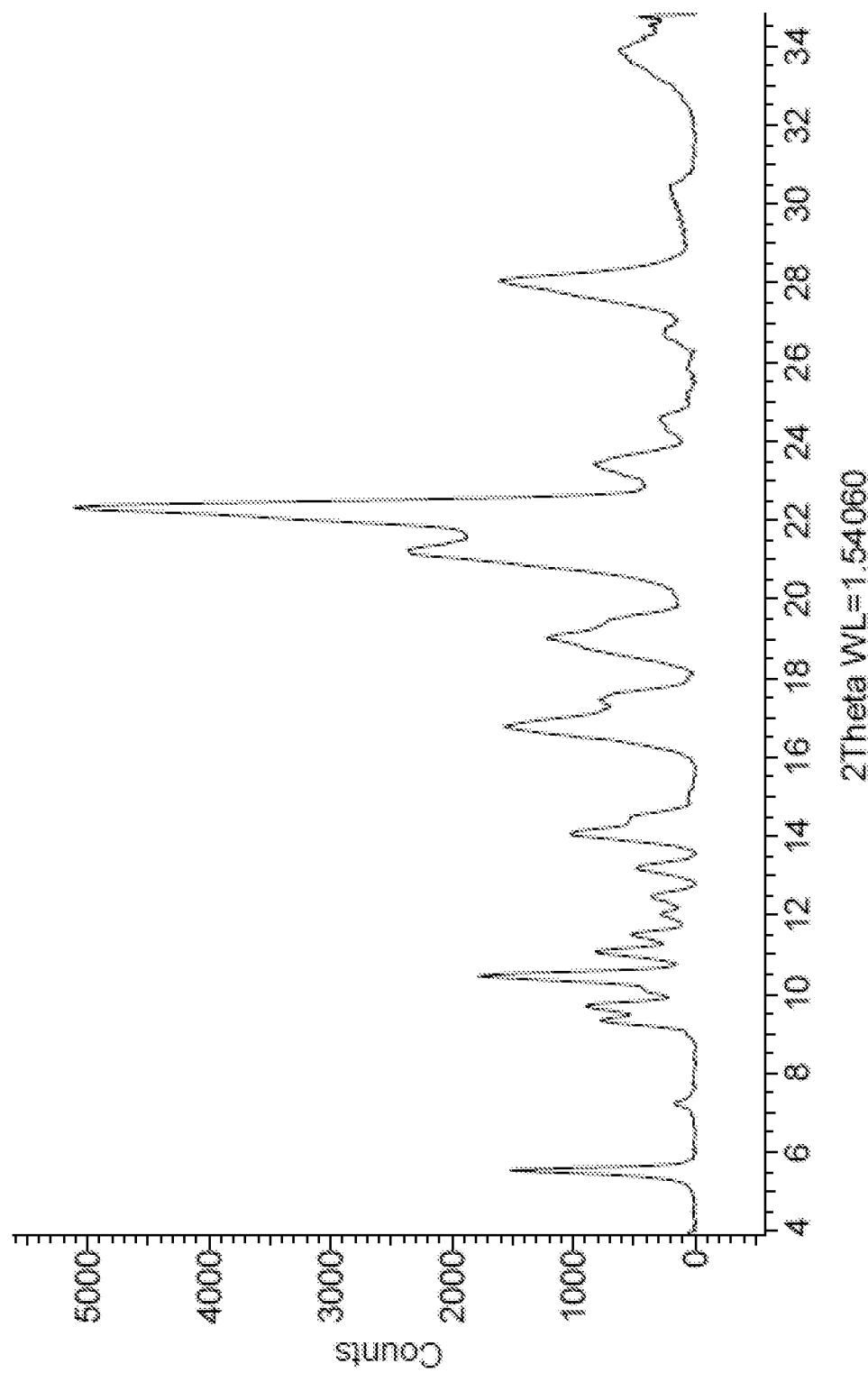
FIG. 3 is a representative PXRD diffractogram of tenofovir alafenamide succinate fumarate (1:0.75:0.25) as prepared in Example 3.

An illustrative PXRD diffractogram of tenofovir alafenamide succinate fumarate Form APO-III, as prepared in Example 3, is shown in FIG. 3. A peak listing, comprising representative peaks from the PXRD diffractogram in FIG. 3, and their relative intensities, is provided in Table 3.

Although illustrative of the PXRD diffractogram that is provided for the tenofovir alafenamide succinate fumarate Form APO-III of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of tenofovir alafenamide succinate fumarate Form APO-III from FIG. 3

| Angle (2θ) | Relative intensity (%) |
|---|---|
| 5.54 | 29.6 |
| 7.23 | 3.4 |
| 9.34 | 15.1 |
| 9.70 | 17.5 |
| 10.46 | 34.9 |
| 11.08 | 15.9 |
| 11.51 | 10.2 |
| 12.02 | 5.4 |
| 12.46 | 7.0 |
| 13.20 | 9.5 |
| 14.06 | 20.0 |
| 14.38 | 10.6 |
| 16.78 | 30.8 |
| 17.46 | 15.3 |
| 19.02 | 23.8 |
| 21.22 | 46.1 |
| 22.32 | 100.0 |
| 28.06 | 31.5 |

Figure 7:
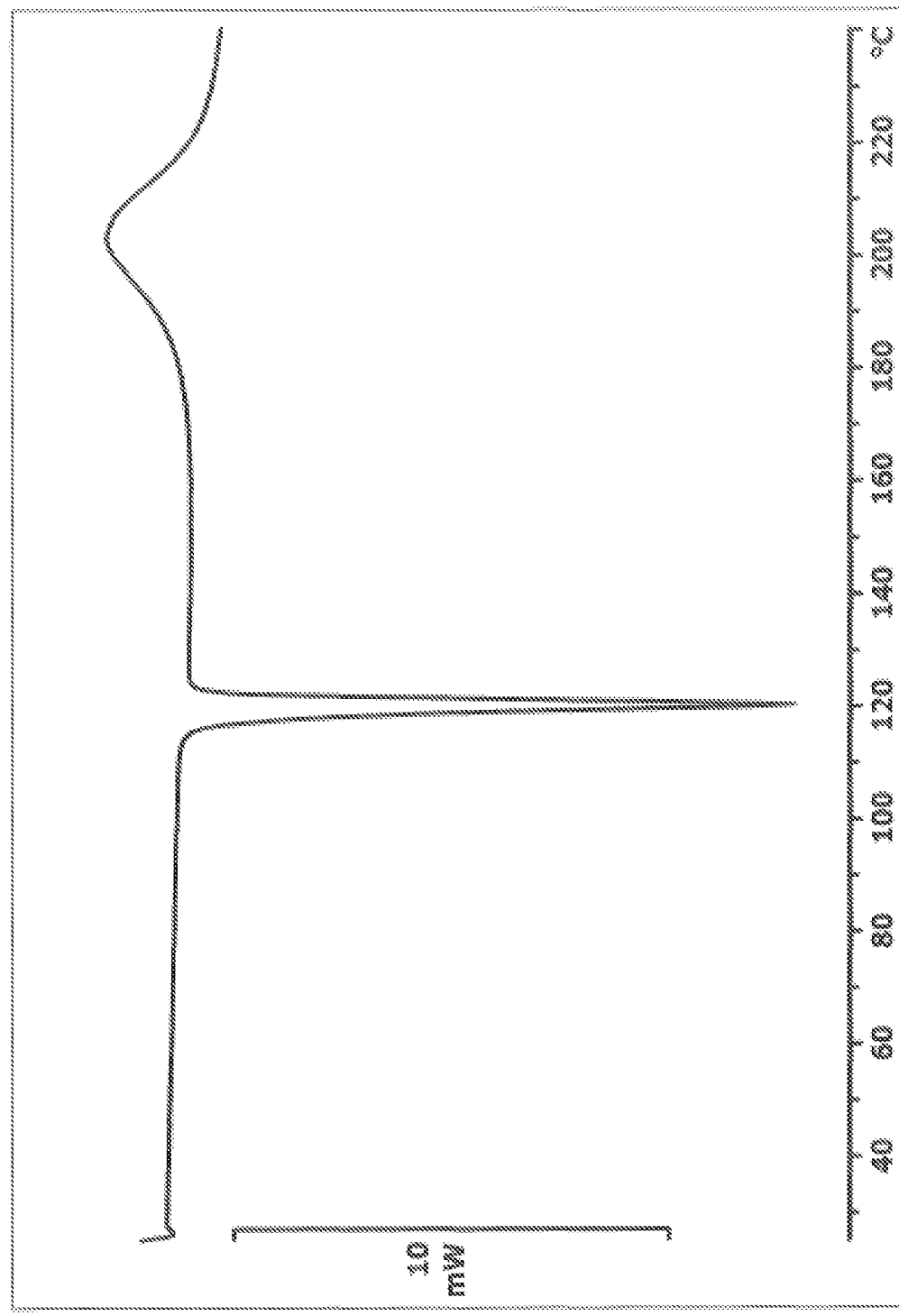
FIG. 7 is a representative DSC thermogram of tenofovir alafenamide succinate fumarate (1:0.75:0.25) as prepared in Example 3.

An illustrative DSC thermogram of tenofovir alafenamide succinate fumarate Form APO-III is shown in FIG. 7. The DSC thermogram may be further characterized by an endothermic peak with a peak onset at approximately 118° C. and a peak maximum at approximately 120° C.

In a fifth embodiment of the present invention, there is provided a crystalline form of tenofovir alafenamide, tenofovir alafenamide succinate malate Form APO-IV, comprising tenofovir alafenamide, succinic acid, and L-malic acid in a molar ratio of approximately 1:0.4:0.4, respectively.

Tenofovir alafenamide succinate malate Form APO-IV can be characterized by a PXRD diffractogram comprising, among other peaks, characteristic peaks, expressed in degrees 2θ (±0.2°), at 5.4°, 9.9° and 15.1°. Preferably, the PXRD diffractogram further comprises at least three peaks, expressed in degrees 2θ (±0.2°), selected from the group consisting of 11.8°, 13.2°, 13.9°, 16.5°, 19.0°, 21.1°, 22.0° and 26.1°. More preferably, the PXRD diffractogram further comprises peaks, expressed in degrees 2θ (±0.2°), at 11.8°, 13.2°, 13.9°, 16.5°, 19.0°, 21.1°, 22.0° and 26.1°.

Figure 4:
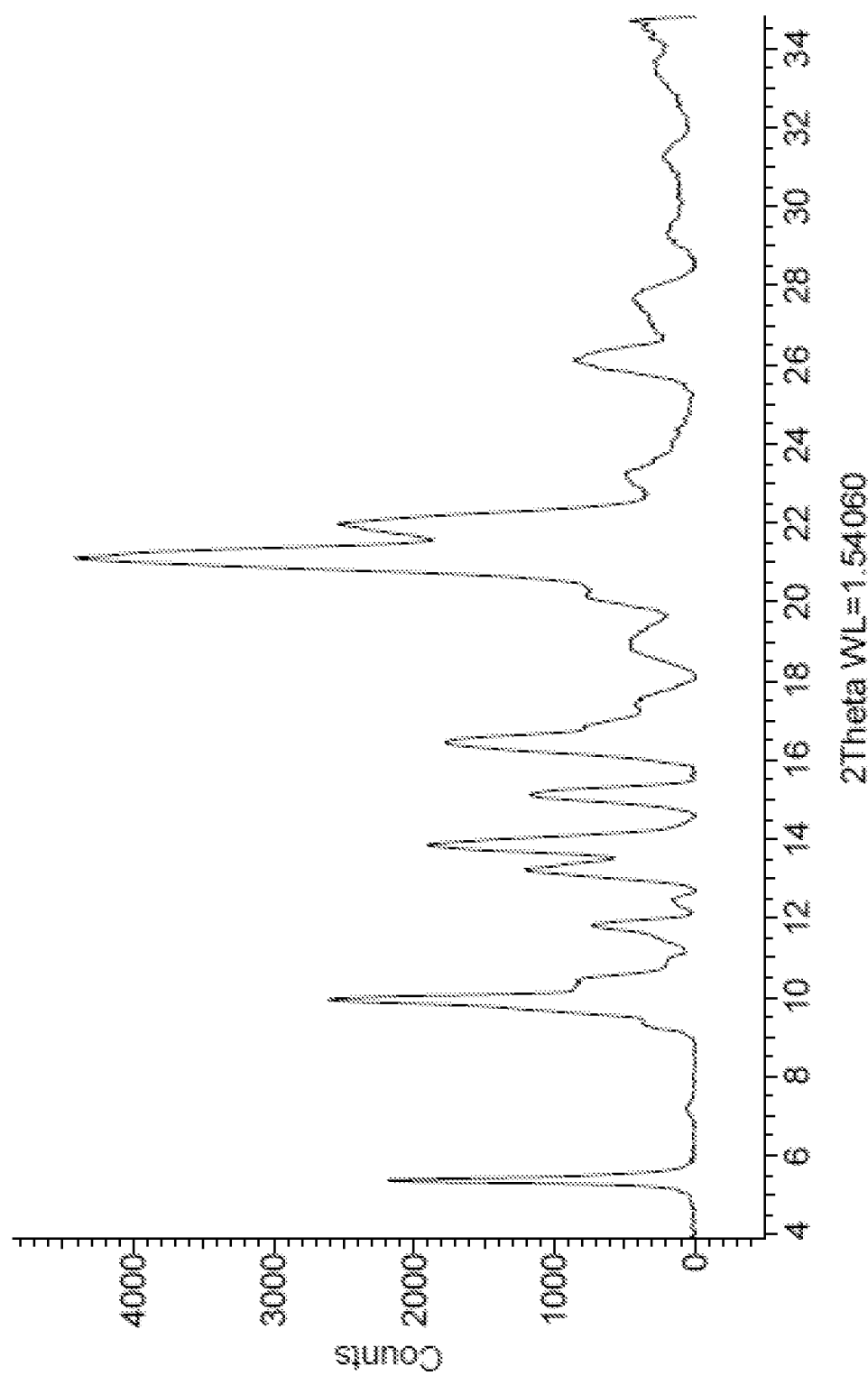
FIG. 4 is a representative PXRD diffractogram of tenofovir alafenamide succinate L-malate (1:0.4:0.4) as prepared in Example 4.

An illustrative PXRD diffractogram of tenofovir alafenamide succinate malate Form APO-IV, as prepared in Example 4, is shown in FIG. 4. A peak listing, comprising representative peaks from the PXRD diffractogram in FIG. 4, and their relative intensities, is provided in Table 4. Although illustrative of the PXRD diffractogram that is provided for the tenofovir alafenamide succinate malate Form APO-IV of the present invention, the relative intensities of the peaks are variable. Thus, depending on a particular sample, the prominence or relative intensity of the peaks observed may differ from those in the illustrative PXRD diffractogram and peak listing.

TABLE 4

Relative peak intensities of tenofovir alafenamide succinate malate Form APO-IV from FIG. 4

| Angle (2θ) | Relative intensity (%) |
|---|---|
| 5.37 | 49.4 |
| 9.95 | 59.1 |
| 11.82 | 16.6 |
| 13.23 | 27.4 |
| 13.86 | 43.2 |
| 15.13 | 26.5 |
| 16.45 | 40.2 |
| 19.03 | 10.4 |
| 21.11 | 100.0 |
| 21.98 | 57.6 |
| 26.12 | 19.6 |

Figure 8:
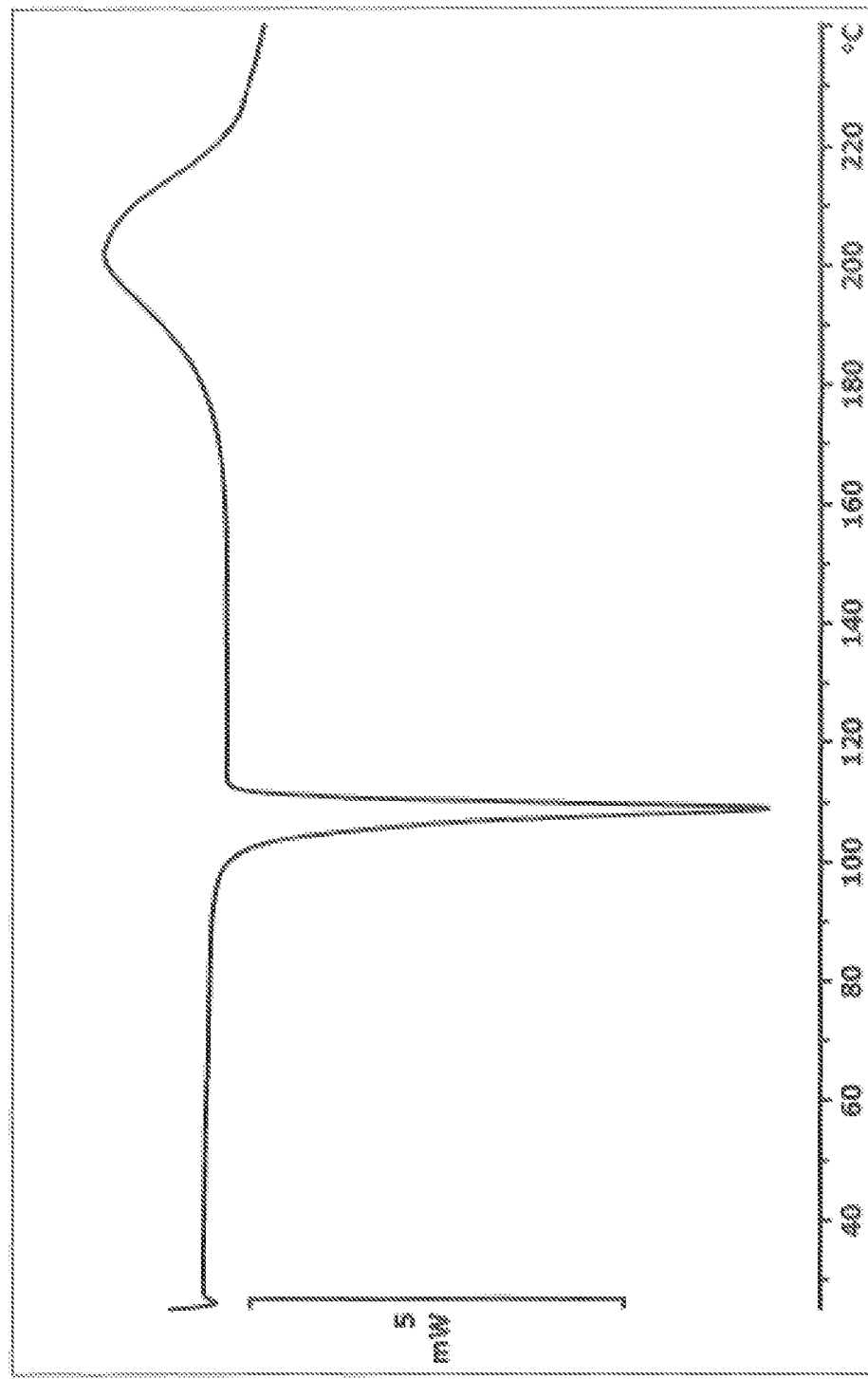
FIG. 8 is a representative DSC thermogram of tenofovir alafenamide succinate L-malate (1:0.4:0.4) as prepared in Example 4.
Figure 9:
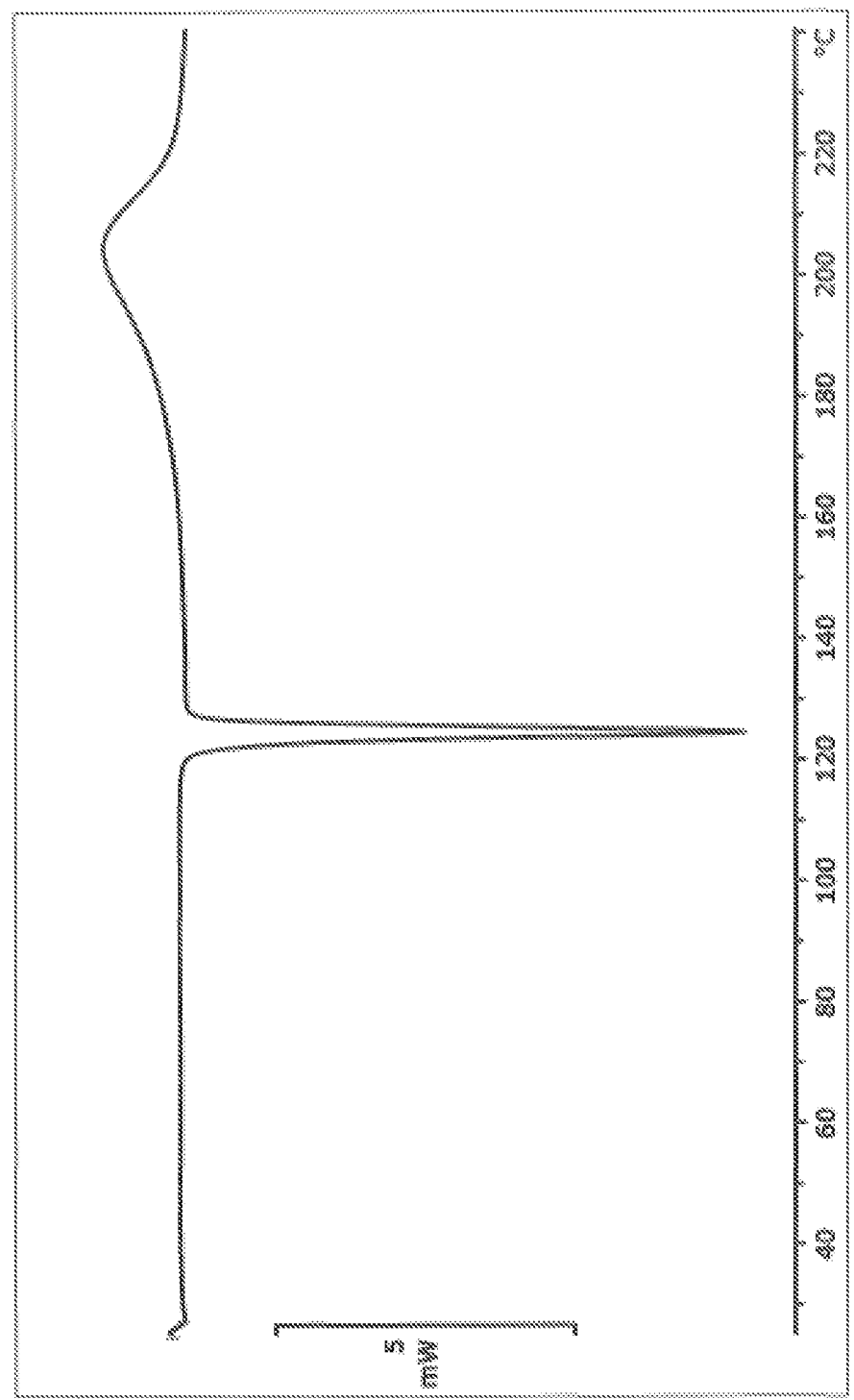
FIG. 9 is a representative DSC thermogram of tenofovir alafenamide fumarate (1:1) showing an endothermic peak with a peak onset at 122.5° C. and a peak maximum at 124.0° C.
Figure 10:
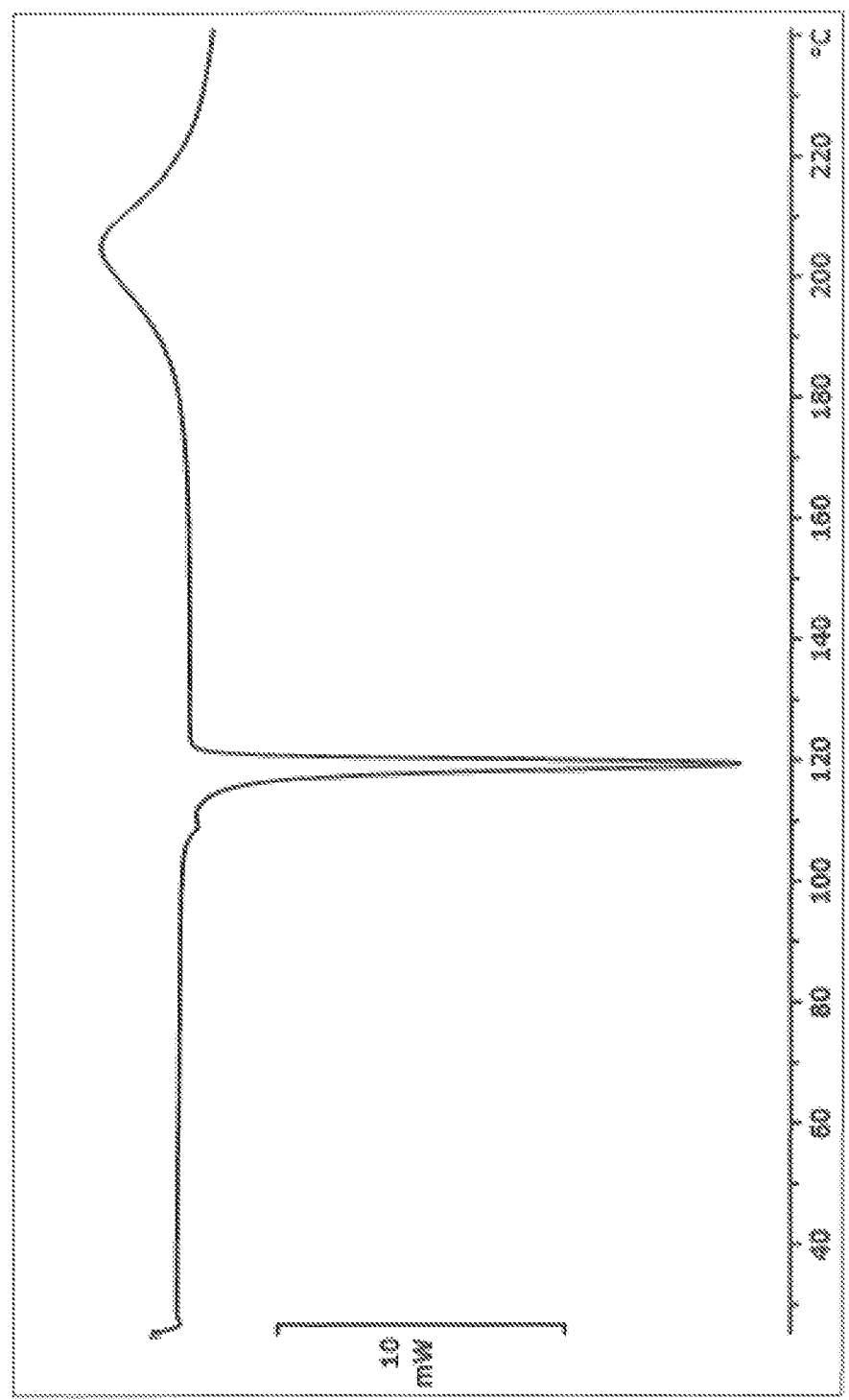
FIG. 10 is a representative DSC thermogram of tenofovir alafenamide succinate (1:1) showing an endothermic peak with a peak onset at 116.9° C. and a peak maximum at 118.6° C.

An illustrative DSC thermogram of tenofovir alafenamide succinate malate Form APO-IV is shown in FIG. 8. The DSC thermogram may be further characterized by an endothermic peak with a peak onset at approximately 105° C. and a peak maximum at approximately 109° C.

In a sixth embodiment of the invention, there is provided a process for the preparation of a crystalline form of tenofovir alafenamide succinate fumarate represented by the following formula:

[TAF][succinic acid]$_{1-x}$[fumaric acid]$_x$ wherein
TAF is tenofovir alafenamide;
x is in the range of 0.05 to 0.95,
the process comprising:
(1) preparing a solution comprising tenofovir alafenamide, succinic acid, and fumaric acid in a relative mole ratio of 1:(1−x):x in a suitable solvent at a suitable temperature to afford a mixture;
(2) cooling the mixture, if necessary, to form a suspension; and
(3) isolating the tenofovir alafenamide succinate fumarate crystals from the suspension.

The step of preparing a solution comprising tenofovir alafenamide, succinic acid, and fumaric acid may involve dissolving tenofovir alafenamide, fumaric acid, and succinic acid in the desired molar ratio in a suitable solvent. Alternatively, tenofovir alafenamide hemifumarate or tenofovir alafenamide monosuccinate may be used as the source of tenofovir alafenamide, with appropriate amounts of tenofovir alafenamide, succinic acid, and fumaric acid used as necessary to adjust the molar ratios of the components to the desired final stoichiometry.

Preferably, the suitable solvent is selected from the group consisting of nitriles such as acetonitrile, esters such as ethyl acetate, and ketones such as acetone. Most preferably, the suitable solvent is acetonitrile. Preferably, the suitable temperature for dissolution is elevated, and is preferably between approximately 60° C. and approximately 80° C.

Following dissolution, the solution can be cooled, preferably to room temperature or lower, if necessary, to afford a suspension. Filtration of the suspension and drying in vacuo, preferably at an elevated temperature between approximately 30° C. and approximately 60° C., affords tenofovir alafenamide succinate fumarate.

In a further embodiment of the invention, there is provided a pharmaceutical composition of a crystalline form of tenofovir alafenamide succinate fumarate comprising tenofovir alafenamide, succinic acid, and fumaric acid, with one or more pharmaceutically acceptable excipients. Preferably, the pharmaceutical composition is a solid dosage form suitable for oral administration, such as a capsule, tablet, pill, powder, or granulate. Most preferably, the pharmaceutical composition is a tablet. Such pharmaceutical compositions typically contain at least about 0.1% by weight of tenofovir alafenamide succinate fumarate. Preferably, the percentage of tenofovir alafenamide succinate fumarate in the compositions is in the range of about 2% to about 60% of the weight of a given unit dosage form. Preferably, the pharmaceutical composition provides a dose of tenofovir alafenamide succinate fumarate that is equivalent to the 10 mg of tenofovir alafenamide that is found in SYMTUZA® drug products or to the 25 mg of tenofovir alafenamide that is found in VEMLIDY®, ODEFSEY®, BIKTARVY®, and DESCOVY® drug products.

Suitable pharmaceutically acceptable excipients are preferably inert with respect to the crystalline form of tenofovir alafenamide succinate fumarate of the present invention, and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP) and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol and lactitol; disintegrants such as croscarmellose sodium, crospovidone, polyvinylpyrrolidone, sodium starch glycollate, corn starch, microcrystalline cellulose, hydroxypropyl methylcellulose and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol and talc; and dispersants or solubility enhancing agents, such cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, antiadherents or glidants may be added as required.

Other suitable excipients and the preparation of solid oral dosage forms is well known to person of skill in the art, and is described generally, for example, in *Remington The Science and Practice of Pharmacy* 21$^{st}$ *Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended release coatings, using standard pharmaceutical coatings. Such coatings, and their application, are well known to persons skilled in the art, and are described, for example, in *Remington The Science and Practice of Pharmacy* 21$^{st}$ *Edition* (Lippincott Williams & Wilkins: Philadelphia; 2006; Chapter 46).

Optionally, pharmaceutical compositions according to the present invention can be prepared with other medicinal ingredients for use in combination therapy. Alternatively, combination therapy using the tenofovir alafenamide succinate fumarate crystalline forms of the present invention can involve individual pharmaceutical compositions for each medicinal ingredient, which are administered concurrently or sequentially.

In one embodiment, when used in combination therapy, a crystalline form of tenofovir alafenamide succinate fumarate of the present invention is used in combination with emtricitabine. In this embodiment of the present invention, there is provided a pharmaceutical composition comprising a fixed dose combination of a crystalline form of tenofovir alafenamide succinate fumarate comprising tenofovir alafenamide, succinic acid, and fumaric acid, with emtricitabine. Pharmaceutical compositions containing a combination of active ingredients may be prepared in the same manner as described above. Preferably, in such fixed dose combinations, the pharmaceutical composition provides doses of tenofovir alafenamide succinate fumarate and emtricitabine that are equivalent to those found in DESCOVY® tablets. Thus, for example, a preferred fixed dose combination tablet may comprise 31 mg of tenofovir alafenamide succinate fumarate (1:0.5:0.5) (providing 25 mg tenofovir alafenamide free base) and 200 mg emtricitabine.

In a further embodiment, when used in combination therapy, a crystalline form of tenofovir alafenamide succinate fumarate of the present invention is used in combination with emtricitabine and rilpivirine hydrochloride. In this embodiment of the present invention, there is provided a pharmaceutical composition comprising a fixed dose combination of a crystalline form of tenofovir alafenamide succinate fumarate comprising tenofovir alafenamide, succinic acid, and fumaric acid, with emtricitabine and rilpivirine hydrochloride. Pharmaceutical compositions containing a combination of active ingredients may be prepared in the same manner as described above. Preferably, in such fixed dose combinations, the pharmaceutical composition provides doses of tenofovir alafenamide succinate fumarate, emtricitabine, and rilpivirine hydrochloride that are equivalent to those found in ODEFSEY® tablets. Thus, for example, a preferred fixed dose combination tablet may comprise 31 mg of tenofovir alafenamide succinate fumarate (1:0.5:0.5) (providing 25 mg tenofovir alafenamide free base), 200 mg emtricitabine, and 27.5 mg rilpivirine hydrochloride (providing 25 mg rilpivirine free base).

In a further embodiment, when used in combination therapy, a crystalline form of tenofovir alafenamide succinate fumarate of the present invention is used in combination with emtricitabine, cobicistat, and darunavir. In this embodiment of the present invention, there is provided a pharmaceutical composition comprising a fixed dose combination of a crystalline form of tenofovir alafenamide succinate fumarate comprising tenofovir alafenamide, succinic acid, and fumaric acid, with emtricitabine, cobicistat, and darunavir. Pharmaceutical compositions containing a combination of active ingredients may be prepared in the same manner as described above. Preferably, in such fixed dose combinations, the pharmaceutical composition provides doses of tenofovir alafenamide succinate fumarate, emtricitabine, cobicistat, and darunavir that are equivalent to those found in SYMTUZA® tablets. Thus, for example, a preferred fixed dose combination tablet may comprise 13 mg of tenofovir alafenamide succinate fumarate (1:0.5:0.5) (providing 10 mg tenofovir alafenamide free base), 200 mg emtricitabine, 150 mg cobicistat, and 800 mg darunavir.

In a further embodiment, when used in combination therapy, a crystalline form of tenofovir alafenamide succinate fumarate of the present invention is used in combination with emtricitabine and bictegravir sodium. In this embodiment of the present invention, there is provided a pharmaceutical composition comprising a fixed dose combination of a crystalline form of tenofovir alafenamide succinate fumarate comprising tenofovir alafenamide, succinic acid, and fumaric acid, with emtricitabine and bictegravir sodium. Pharmaceutical compositions containing a combination of active ingredients may be prepared in the same manner as described above. Preferably, in such fixed dose combinations, the pharmaceutical composition provides doses of tenofovir alafenamide succinate fumarate, emtricitabine, and bictegravir sodium that are equivalent to those found in BIKTARVY® tablets. Thus, for example, a preferred fixed dose combination tablet may comprise 31 mg of tenofovir alafenamide succinate fumarate (1:0.5:0.5) (providing 25 mg tenofovir alafenamide free base), 200 mg emtricitabine, and 52.5 mg bictegravir sodium (providing 50 mg bictegravir free acid).

EXAMPLES

The following non-limiting examples are illustrative of some of the aspects and embodiments of the invention described herein.

The tenofovir alafenamide hemifumarate used as a starting material in the following examples was consistent with the form reported in WO 2013/025788 A1. Other forms are equally suitable as starting material, provided dissolution of the form occurs when preparing the novel crystalline forms of tenofovir alafenamide of the present invention.

PXRD Analysis:

PXRD diffractograms were recorded on a Bruker D8 Discover powder X-ray diffractometer (Bruker-AXS, Karlsruhe, Germany). The generator was a Micro-focus X-ray source (IMSTube: Cu tube with 1.54060 Å) with a voltage of 50 kV and current of 1.00 mA, using a divergence slit of 0.3 mm and collimator of 0.3 mm. For each sample, one frame was collected using a still scan with a Pilatus 3R-100 kA detector at the distance of 154.72 mm from the sample. Raw data were evaluated using the program EVA (Bruker-AXS, Karlsruhe, Germany).

Differential Scanning Calorimetry Analysis:

DSC thermograms were collected on a Mettler-Toledo 821 e instrument. Samples (2±0.2 mg) was weighed into a 40 µL aluminum pan and was crimped closed with an aluminum lid having a 50 µm perforation. The sample was analyzed under a flow of nitrogen (50±5 mL/min) at a scan rate of 10° C./minute between 25° C. and 360° C.

Example 1: Preparation of Tenofovir Alafenamide Succinate Fumarate Form APO-1

Tenofovir alafenamide hemifumarate (535 mg), fumaric acid (28 mg), and succinic acid (33 mg) were suspended in acetonitrile (10 mL) and heated to 65° C. Once a solution was obtained, heating was discontinued, and the solution was stirred at ambient temperature for approximately 18 hours. The solids were collected by filtration, washed with acetonitrile (2×1 mL) and dried under vacuum at 40° C. for 24 hours to afford tenofovir alafenamide succinate fumarate Form APO-1 as a white solid (545 mg). The PXRD diffractogram and DSC thermogram of a sample prepared by this method are shown in FIG. 1 and FIG. 5, respectively. $^1$H NMR analysis of the solid (DMSO-$d_6$) identified a molar ratio of tenofovir alafenamide to succinic acid to fumaric acid of 1:0.25:0.75.

$^1$H-NMR of tenofovir alafenamide succinate fumarate Form APO-1 (DMSO-$d_6$, 400 MHz) δ: 8.14 (s, 1H), 8.10 (s, 1H), 7.29 (t, J=7.8 Hz, 2H), 7.20 (br s, 2H), 7.13 (t, J=7.3 Hz, 1H), 7.05 (d, J=8.3 Hz, 2H), 6.64 (s, 1.5H), 5.62 (t, J=11.2 Hz, 1H), 4.85 (sep, J=6.2 Hz, 1H), 4.28 (dd, J=3.7, 14.3 Hz, 1H), 4.14 (dd, J=6.5, 14.3 Hz, 1H), 3.98-3.90 (m, 1H), 3.89-3.82 (m, 2H), 3.76 (dd, J=9.8, 13.4 Hz, 1H), 2.42 (s, 1H), 1.15 (d, J=6.4 Hz, 6H), 1.13 (d, overlapping 1.15 signal, 3H), 1.07 (d, J=6.2 Hz, 3H).

Example 2: Preparation of Tenofovir Alafenamide Succinate Fumarate Form APO-II Tenofovir alafenamide hemifumarate (546 mg) and succinic acid (63 mg) were suspended in acetonitrile (10 mL) and heated to 65° C. Once a solution was obtained, heating was discontinued, and the solution was stirred at ambient temperature for approximately 18 hours. The solids were collected by filtration, washed with acetonitrile (2×1 mL) and dried under vacuum at 45° C. for 24 hours to afford tenofovir alafenamide succinate fumarate Form APO-II as a white solid (562 mg). The PXRD diffractogram and DSC thermogram of a sample prepared by this method are shown in FIG. 2 and FIG. 6, respectively. $^1$H NMR analysis of the solid (DMSO-$d_6$) identified a molar ratio of tenofovir alafenamide to succinic acid to fumaric acid of 1:0.5:0.5.

$^1$H-NMR of tenofovir alafenamide succinate fumarate Form APO-II (DMSO-$d_6$, 400 MHz) δ: 8.14 (s, 1H), 8.10 (s, 1H), 7.29 (t, J=7.8 Hz, 2H), 7.20 (br s, 2H), 7.13 (t, J=7.3 Hz, 1H), 7.05 (d, J=8.3 Hz, 2H), 6.64 (s, 1H), 5.62 (t, J=11.2 Hz, 1H), 4.85 (sep, J=6.2 Hz, 1H), 4.28 (dd, J=3.7, 14.3 Hz, 1H), 4.14 (dd, J=6.5, 14.3 Hz, 1H), 3.98-3.90 (m, 1H), 3.89-3.82 (m, 2H), 3.76 (dd, J=9.8, 13.4 Hz, 1H), 2.42 (s, 2H), 1.15 (d, J=6.4 Hz, 6H), 1.13 (d, overlapping 1.15 signal, 3H), 1.07 (d, J=6.2 Hz, 3H).

Example 3: Preparation of Tenofovir Alafenamide Succinate Fumarate Form APO-III Tenofovir alafenamide hemifumarate (270 mg), Tenofovir alafenamide free base (244 mg), and succinic acid (90 mg) were suspended in acetonitrile (10.0 mL) and heated to 65° C. Once a solution was obtained, heating was discontinued, and the solution was stirred at ambient temperature for approximately 18 hours. The solids were collected by filtration, washed with acetonitrile (2×1 mL) and dried under vacuum at 40° C. for 24 hours to afford tenofovir alafenamide succinate fumarate Form APO-III as a white solid (541 mg). The PXRD diffractogram and DSC thermogram of a sample prepared by this method are shown in FIG. 3 and FIG. 7, respectively. $^1$H NMR analysis of the solid (DMSO-$d_6$) identified a molar ratio of tenofovir alafenamide to succinic acid to fumaric acid of 1:0.75:0.25.

$^1$H-NMR of tenofovir alafenamide succinate fumarate Form APO-III (DMSO-$d_6$, 400 MHz) δ: 8.14 (s, 1H), 8.10 (s, 1H), 7.29 (t, J=7.8 Hz, 2H), 7.20 (br s, 2H), 7.13 (t, J=7.3 Hz, 1H), 7.05 (d, J=8.3 Hz, 2H), 6.63 (s, 0.5H), 5.62 (t, J=11.2 Hz, 1H), 4.85 (sep, J=6.2 Hz, 1H), 4.28 (dd, J=3.7, 14.3 Hz, 1H), 4.14 (dd, J=6.5, 14.3 Hz, 1H), 3.98-3.90 (m, 1H), 3.89-3.82 (m, 2H), 3.76 (dd, J=9.8, 13.4 Hz, 1H), 2.42 (s, 3H), 1.15 (d, J=6.4 Hz, 6H), 1.13 (d, overlapping 1.15 signal, 3H), 1.07 (d, J=6.2 Hz, 3H).

Example 4: Preparation of Tenofovir Alafenamide Succinate Malate Form APO-IV Tenofovir alafenamide free base (486 mg), L-malic acid (69 mg), and succinic acid (58 mg) were suspended in acetonitrile (10 mL) and heated to 70° C. Once a solution was obtained, heating was discontinued, and the solution was stirred at ambient temperature for approximately 18 hours. The solids were collected by filtration, washed with acetonitrile (1 mL) and dried under vacuum at 50° C. for 24 hours to afford tenofovir alafenamide succinate malate Form APO-IV as a white solid (473 mg). The PXRD diffractogram and DSC thermogram of a sample prepared by this method are shown in FIG. 4 and FIG. 8, respectively. $^1$H NMR analysis of the solid (DMSO-$d_6$) identified a molar ratio of tenofovir alafenamide to succinic acid to L-malic acid of 1:0.36:0.39.

$^1$H-NMR of tenofovir alafenamide succinate malate Form APO-IV (DMSO-$d_6$, 400 MHz) δ: 8.14 (s, 1H), 8.10 (s, 1H), 7.29 (t, J=7.8 Hz, 2H), 7.20 (br s, 2H), 7.13 (t, J=7.3 Hz, 1H), 7.05 (d, J=8.3 Hz, 2H), 5.62 (t, J=11.2 Hz, 1H), 4.85 (sep, J=6.2 Hz, 1H), 4.30-4.22 (m, 1.4H), 4.14 (dd, J=6.5, 14.3 Hz, 1H), 3.98-3.90 (m, 1H), 3.89-3.82 (m, 2H), 3.76 (dd, J=9.8, 13.4 Hz, 1H), 2.61 (dd, J=4.9, 15.7 Hz, 0.4H), 2.43 (dd, J=7.8, 15.6 Hz, 0.4H), 2.42 (s, overlapping 2.43 signal, 1.4H), 1.15 (d, J=6.4 Hz, 6H), 1.13 (d, overlapping 1.15 signal, 3H), 1.07 (d, J=6.2 Hz, 3H).

Example 5: Comparative Intrinsic Dissolution Testing

Intrinsic dissolution rate (IDR) measurements were performed using a Wood apparatus (Pharma Test PT-DT8 instrument) having a bath temperature of 37° C. Samples were prepared by compressing 200-400 mg samples at 1.5 metric tons for 1 minute. A dissolution medium consisting of 900 mL distilled water, and rotation speed of 50 rpm, was used for each experiment. Results are provided in Table 5.

TABLE 5

Comparative intrinsic dissolution rates for the crystalline forms of the invention with tenofovir alafenamide fumarate (1:1) and tenofovir alafenamide succinate (1:1)

| Form | Intrinsic Dissolution Rate (mg min$^{-1}$ cm$^{-2}$) |
|---|---|
| Tenofovir alafenamide succinate fumarate Form APO-I | 1.11 |
| Tenofovir alafenamide succinate fumarate Form APO-II | 1.22 |
| Tenofovir alafenamide succinate fumarate Form APO-III | 1.14 |
| Tenofovir alafenamide succinate malate Form APO-IV | 1.39 |
| Tenofovir alafenamide fumarate (1:1) | 0.87 |
| Tenofovir alafenamide succinate (1:1) | 0.67 |

What is claimed is:

1. A crystalline form of tenofovir alafenamide succinate fumarate comprising tenofovir alafenamide, succinic acid, and fumaric acid.

2. The crystalline form of tenofovir alafenamide of claim 1, wherein the molar ratio of tenofovir alafenamide to (succinic acid+fumaric acid) is approximately 1:1.

3. The crystalline form of claim 2, wherein the crystalline form is represented by the following formula:

[TAF][succinic acid]$_{1-x}$[fumaric acid]$_x$ wherein
  TAF is tenofovir alafenamide; and
  x is in the range of 0.05 to 0.95.

4. The crystalline form of claim 2, wherein the molar ratio of tenofovir alafenamide to succinic acid to fumaric acid is approximately 1:0.25:0.75 and the crystalline form is characterized by a PXRD diffractogram comprising peaks, expressed in degrees 2θ (±0.2°), at 5.6°, 10.5° and 22.4°.

5. The crystalline form of claim 4, further comprising at least three peaks in the PXRD diffractogram, expressed in degrees 2θ(±0.2°), selected from the group consisting of: 9.4°, 9.7°, 11.1°, 11.5°, 13.3°, 14.1°, 16.9°, 17.6°, 19.1° and 28.2°.

6. The crystalline form of claim 4, characterized by a DSC thermogram comprising an endothermic peak with a peak onset at approximately 119° C. and a peak maximum at approximately 120° C.

7. The crystalline form of claim 2, wherein the molar ratio of tenofovir alafenamide to succinic acid to fumaric acid is approximately 1:0.5:0.5 and the crystalline form is characterized by a PXRD diffractogram comprising peaks, expressed in degrees 2θ (±0.2°), at 5.6°, 10.5° and 22.2°.

8. The crystalline form of claim 7, further comprising at least three peaks in the PXRD diffractogram, expressed in degrees 2θ (±0.2°), selected from the group consisting of: 7.2°, 9.4°, 9.7°, 11.1°, 11.5°, 13.2°, 14.1°, 16.7°, 18.9° and 27.8°.

9. The crystalline form of claim 7, characterized by a DSC thermogram comprising an endothermic peak with a peak onset at approximately 118° C. and a peak maximum at approximately 120° C.

10. The crystalline form of claim 2, wherein the molar ratio of tenofovir alafenamide to succinic acid to fumaric acid is approximately 1:0.75:0.25 and the crystalline form is characterized by a PXRD diffractogram comprising peaks, expressed in degrees 2θ (±0.2°), at 5.5°, 10.5° and 22.3°.

11. The crystalline form of claim 10, further comprising at least three peaks in the PXRD diffractogram, expressed in degrees 2θ (±0.2°), selected from the group consisting of: 7.2°, 9.3°, 9.7°, 11.1°, 11.5°, 13.2°, 14.1°, 16.8°, 19°, and 28.1°.

12. The crystalline form of claim 10, characterized by a DSC thermogram comprising an endothermic peak with a peak onset at approximately 118° C. and a peak maximum at approximately 120° C.

13. A crystalline form of tenofovir alafenamide succinate malate comprising tenofovir alafenamide, succinic acid, and L-malic acid.

14. The crystalline form of claim 13, wherein the molar ratio of tenofovir alafenamide to succinic acid to L-malic acid is approximately 1:0.4:0.4 and the crystalline form is characterized by a PXRD diffractogram comprising peaks, expressed in degrees 2θ (±0.2°), at 5.4°, 9.9° and 15.1°.

15. The crystalline form of claim 14, further comprising at least three peaks in the PXRD diffractogram, expressed in degrees 2θ (±0.2°), selected from the group consisting of: 11.8°, 13.2°, 13.9°, 16.5°, 19.0°, 21.10° 22.0° and 26.1°.

16. The crystalline form of claim 14, characterized by a DSC thermogram comprising an endothermic peak with a peak onset at approximately 105° C. and a peak maximum at approximately 109° C.

17. A pharmaceutical composition comprising a crystalline form of tenofovir alafenamide succinate fumarate according to claim 2, and one or more pharmaceutically acceptable excipients.

18. The pharmaceutical composition of claim 17, further comprising an additional therapeutic agent selected from the group consisting of emtricitabine, darunavir, cobicistat, bictegravir, and rilpivirine.

19. A method for treating a human immunodeficiency virus (HIV) infection or a hepatitis B virus (HBV) infection comprising administering an effective amount of the crystalline form of tenofovir alafenamide succinate fumarate of claim 2.

20. The method of claim 19, wherein the tenofovir alafenamide succinate fumarate is used in combination with an additional therapeutic agent selected from the group consisting of emtricitabine, darunavir, cobicistat, bictegravir, and rilpivirine.

* * * * *